United States Patent [19]

Dukat et al.

[11] Patent Number: 5,254,772
[45] Date of Patent: Oct. 19, 1993

[54] CHEMICAL PROCESS

[75] Inventors: Wolfgang W. Dukat, Konigstein, Fed. Rep. of Germany; John H. Holloway, Leicester; Eric G. Hope, Warwickshire, both of England; Matthias Rieland, Hanover, Fed. Rep. of Germany; Paul J. Townson, Lancashire; Richard L. Powell, Cheshire, both of England

[73] Assignee: Imperial Chemical Industries PLC, London, England

[21] Appl. No.: 849,604

[22] Filed: Mar. 12, 1992

[30] Foreign Application Priority Data

Mar. 12, 1991 [GB] United Kingdom ............... 9105167

[51] Int. Cl.$^5$ .................. C07C 17/20; C07C 17/00
[52] U.S. Cl. .................................. 570/170; 570/123
[58] Field of Search ..................... 570/170, 168, 123

[56] References Cited

U.S. PATENT DOCUMENTS 2,423,045 9/1943 Passino et al.
2,759,026 2/1950 McCleary.
3,235,608 3/1962 Gibbs.
3,972,953 8/1976 Lyons.

FOREIGN PATENT DOCUMENTS 705927 3/1965 Canada ........................ 570/170
0164798 12/1985 European Pat. Off. .

Primary Examiner—Alan Siegel
Attorney, Agent, or Firm—Cushman, Darby & Cushman

[57] ABSTRACT

A process for the preparation of an alkane containing fluorine by contacting a halogenated alkane containing at least one hydrogen atom and at least one halogen atom selected from chlorine, bromine and iodine with a transition metal fluoride selected from osmium hexafluoride, iridium hexafluoride, rhenium hexafluoride, ruthenium pentafluoride, chromium pentafluoride, vanadium pentafluoride, rhenium heptafluoride and uranium hexafluoride, whereby to replace at least one hydrogen atom or at least one chlorine, bromine or iodine atom in said halogenated alkane starting material by a fluorine atom.

Use of certain of the defined transition metal fluorides, e.g. $OsF_6$, $IrF_6$ and $ReF_6$ allows the selective replacement of halogen by fluorine, while others, e.g. $UF_6$, $VF_5$ and $ReF_7$ allow selective replacement of hydrogen by fluorine.

8 Claims, No Drawings

CHEMICAL PROCESS

This invention relates to a process for the fluorination of aliphatic compounds, and more particularly to a process for the replacement by fluorine of at least one hydrogen atom and/or at least one halogen atom other than fluorine in aliphatic compounds.

It is already known to manufacture aliphatic compounds containing fluorine by reacting aliphatic chlorocarbons or chlorohydrocarbons with fluorinating agents such as antimony pentafluoride. In many cases, however, known fluorinating agents do not give entirely satisfactory results, being somewhat deficient in activity and/or in product selectivity.

It has now been found that certain transition metal fluorides are useful fluorinating agents capable of selectively replacing by fluorine one or more hydrogen atoms and/or one or more halogen atoms other than fluorine in aliphatic compounds.

According to the present invention there is provided a process for the preparation of an alkane containing fluorine which comprises contacting a halogenated alkane containing at least one hydrogen atom and at least one halogen atom selected from chlorine, bromine and iodine with a transition metal fluoride selected from osmium hexafluoride, iridium hexafluoride, rhenium hexafluoride, ruthenium pentafluoride, chromium pentafluoride, vanadium pentafluoride, rhenium heptafluoride and uranium hexafluoride, and replacing at least one hydrogen atom or at least one one chlorine, bromine or iodine atom in said halogenated alkane by a fluorine atom.

Halogenated alkanes which may be employed in the process of the invention may contain one or more carbon atoms, for example, typically up to 6 carbon atoms, and have at least one hydrogen atom and at least one replaceable halogen atom selected from chlorine, bromine and iodine. Other atoms, for example fluorine, may also be present.

Especially useful halogenated alkanes include hydrochlorocarbons and chlorofluorohydrocarbons.

Specific examples of halogenated alkanes which may be used include dichloromethane, chlorofluoromethane, dibromomethane, bromofluoromethane, and 2-chloro-1,1,1-trifluoroethane from which the products may be respectively difluoromethane, and 1,1,1,2-tetrafluoroethane.

In operating the process of the invention, the halogenated alkane may be contacted with the transition metal fluoride at a temperature at which the halogenated alkane is in the liquid phase or the vapour phase but conveniently the liquid phase. Accordingly the temperature may be from about −80 to about 25° C. depending upon the boiling point of the halogenated alkane, although the reaction proceeds, and may be conducted at, temperatures higher than 25° C., for example up to 100° C., in which case the halogenated alkane may be in the vapour phase. The process of the invention is preferably operated under substantially anhydrous conditions, and is conveniently operated at atmospheric pressure, although superatmospheric or subatmospheric pressures may be employed, if desired.

The transition metal fluoride may, at the reaction temperature, be present in the reaction vessel in the solid or vapour phase, and may be supported on a substrate, for example aluminium fluoride or carbon.

The proportions of halogenated alkane and transition metal fluoride are not critical; either may be in excess over stochiometric, if desired. Thus, for example, the proportion of halogenated alkane to transition metal fluoride may be in the range from about 50:1 to about 1:50, and preferably in the range from about 20:1 to about 1:20 of the stoichiometrically required proportion, although these ranges are given merely by way of guidance and are in no way limiting on the process of the present invention. Hydrogen fluoride may also be included in the reaction mixture as a fluorinating agent, the metal fluoride then optionally being employed in a catalytic amount.

In operating the process of the invention, whether at least one hydrogen atom or at least one halogen atom other than fluorine, or both hydrogen and halogen in the halogenated alkane is/are replaced by fluorine may depend to a large extent on the particular halogenated alkane and on the particular transition metal fluoride used.

Where it is desired to replace at least one halogen atom in the halogenated alkane, the preferred transition metal fluorides are $OsF_6$, $IrF_6$ and $ReF_6$. The use of these particular fluorides allows the replacement of halogen atom other than fluorine in the halogenated alkane by fluorine with a selectivity which may be as high as 80% and even as high as 95%, in particular where $OsF_6$ is used.

Where it is desired to replace a hydrogen atom in the halogenated alkane and the halogenated alkane is a chlorinated alkane, the preferred transition metal fluorides are $UF_6$, $VF_5$ and $ReF_7$. The use of these particular fluorides allows the replacement of at least one hydrogen atom by fluorine with a selectivity which may be as high as 80% and even as high as 95%, in particular where $UF_6$ is used.

Furthermore, certain of the transition metal fluorides, for example $RuF_5$, may selectively replace at least one hydrogen atom in certain halogenated alkanes, for example $CF_3CH_2Cl$, yet selectively replace at least one halogen atom other than fluorine in other halogenated alkanes, for example in dichloromethane. $CrF_5$ may selectively replace at least one hydrogen atom although the selectivity may be better with certain halogenated alkane starting materials than with others; for example high selectivity is obtained with $CrF_5$ for the replacement of hydrogen in $CF_3CH_2Cl$ although selectivity may not be as high with $CH_2Cl_2$. In addition, $ReF_7$ may selectively replace at least one hydrogen atom where the halogenated alkane is a chlorinated alkane, but may selectively replace at least one halogen atom where the halogenated alkane is a brominated alkane.

The process of the invention is of particular value for the preparation of difluoromethane from dichloromethane or chlorofluoromethane and accordingly in a preferred aspect of the invention there is provided a process for the preparation of difluoromethane which process comprises contacting dichloromethane or chlorofluoromethane with a transition metal fluoride selected from $OsF_6$, $IrF_6$, $ReF_6$ and $RuF_5$ and maintaining the contact until at least a portion of the dichloromethane or chlorofluoromethane has been converted to difluoromethane. The reaction mixture may, if desired, also contain hydrogen fluoride.

The process of the invention is also of particular value for the preparation of 1,1,1,2-tetrafluoroethane from 2-chloro-1,1,1-trifluoroethane and accordingly in a further aspect of the invention there is provided a process for the preparation of 1,1,1,2-tetrafluoroethane which comprises contacting 2-chloro-1,1,1-trifluoroethane with a transition metal fluoride selected from $OsF_6$, $IrF_6$, and $ReF_6$ and maintaining the contact until at least a portion of the 2-chloro-1,1,1-trifluoroethane has been converted to 1,1,1,2-tetrafluoroethane. The reaction mixture may, if desired, also contain hydrogen fluoride.

The process of the invention is also of particular value for the preparation of dichlorofluoromethane by contacting dichloromethane with $ReF_7$, $UF_6$ or $VF_5$ and of 2-chloro-1,1,1,2-tetrafluoroethane by contacting 2-chloro-1,1,1-trifluoroethane with $RuF_5$, $ReF_7$, $CrF_5$, $VF_5$ or $UF_6$ and these processes represent further particular embodiments of the invention.

The invention is illustrated by the following examples in which the organic materials were handled in a vacuum line made from stainless steel tubing with stainless steel valves and the metal fluorides were handled in satellite lines made from PTFE. Reactions were conducted in FEP tubes (copolymer of HFP and TFE) which could be sealed thermally in a small ring furnace after reaction had reached completion and could be inserted into a standard precision 5 mm n.m.r. glass tube with a thin film of the lock substance-$d_6$ acetone placed between the tubes. To obtain a reliable integration of $^1H$ against $^{19}F$ signals, $CF_3CH_2OH$ (33% v/v) was added to the lock substance.

All equipment was seasoned with fluorine gas at a pressure of 700-800 mbar for about 16 hours. The transition metal fluorides were prepared by conventional literature methods and were stored in $F_2$ passivated Ni cylinders.

The products were analysed by n.m.r. spectroscopy on a Bruker FT spectrometer AM 300 ($^1H$ at 300.0 MHz, $^{19}F$ at 282,4 MHz) with a 5 mm bore selective probe.

EXAMPLE 1.

Fluorination of $CH_2Cl_2$ by $OsF_6$

A 15 cm long×4 mm diameter (outside diameter)×0.5 mm wall thickness FEP tube was connected via a PTFE valve (supplied by Production Techniques) to an all metal vacuum line, evacuated to $<10^{-5}$ Torr, passivated with $F_2$ gas (400 Torr) for 20 minutes, and re-evacuated. The valve was closed and the weight of the valve and tube measured.

37.9 mg (0.125 mmol) of $OsF_6$ (prepared in accordance with J. Chem Soc., Dalton Trans., 1988, 1341) was condensed from the nickel storage cylinder into the pre-fluorinated FEP tube by vacuum transfer at $-196°$ C. as follows. The Ni storage container and FEP tube were connected to the vacuum line. The connections were evacuated, passivated with $F_2$ gas and re-evacuated. The FEP tube was cooled to $-196°$ C. in liquid nitrogen and the valves to the FEP tube and Ni storage container were opened to allow the $OsF_6$ to sublime into the FEP tube. The valve to the storage container was closed and the apparatus was re-evacuated, the valve to the FEP tube closed and the FEP tube allowed to warm to room temperature. The FEP tube and valve were taken off the vacuum line and re-weighed.

The FEP tube containing $OsF_6$ and a glass storage vessel containing dried $CH_2Cl_2$ were connected to the vacuum line via a PTFE T-piece. The connectors and T-piece were evacuated, passivated with $R_2$ and re-evacuated.

236 mg, 2.78 mmol of $CH_2Cl_2$ was sublimed into the FEP tube cooled to $-196°$ C. in liquid nitrogen. The PTFE valve was closed and the reaction mixture allowed to warm slowly to $-78°$ C. in a dry-ice-acetone bath and then to room temperature (20° C.) with frequent shaking. After 1 hour the solution had turned from its original yellow colour to black and there was a black precipitate. The FEP tube and PTFE valve were taken off the vacuum line and re-weighed.

The FEP reaction tube and a second FEP tube were connected to the vacuum line via a PTFE T-piece, and the connectors and T-piece were evacuated, passivated with $F_2$ and re-evacuated. The second FEP tube was cooled to $-196°$ C. in liquid nitrogen, the PTFE valves opened and the volatile product from the reaction tube was allowed to sublime into the second FEP tube. The involatile precipitate in the reaction tube was taken for elemental analysis, and was determined to be $OsCl_5$.

The FEP tube containing the volatile product was kept cold at $-196°$ C. and was placed in a small ring furnace and heated gently to form a vacuum and pressure tight seal. The n.m.r. spectra of the volatile product was run at 298 K.

The results are shown in Table 1. From these results it was calculated that the replacement of chlorine by fluorine was 87% selective and that the overall yield of fluorinated products was 88%.

EXAMPLE 2

Fluorination of $CH_2Cl_2$ by $IrF_6$

The procedure described in example 1 was followed except that 39.2 mg, 0.128 mmol of $IrF_6$ (prepared as described in J. Chem Physics., 1970, 53, 1411) and 190 mg, 2.23 mmol of $CH_2Cl_2$ were sublimed into the reaction tube.

The results are shown in Table 1. From these results it was calculated that the replacement of chlorine by fluorine was 78% selective.

EXAMPLE 3

Fluorination of $CH_2Cl_2$ by $ReF_6$

The procedure described in example 1 was followed except that 32.2 mg, 0.107 mmol of $ReF_6$ (prepared as described in J. Chem Soc. Dalton Trans., 1988, 1341) and 475 mg, 5.6 mmol of $CH_2Cl_2$ were sublimed into the reaction tube. The reaction was allowed to run for 5 days before analysis by n.m.r. was carried out. Furthermore, after 5 days no precipitate had formed and the FEP reaction tube itself was sealed as described in example 1 without transferring the volatile products to a second FEP tube.

The results are shown in Table 1. From these results it was calculated that the replacement of chlorine by fluorine was 88.5% selective and that the overall yield of fluorinated products was 95%.

EXAMPLE 4

Fluorination of $CH_2Cl_2$ by $RuF_5$

The procedure described in example 1 was followed except that 60.8 mg, 0.310 mmol of solid $RuF_5$ (prepared as described in J. Chem Soc., 1963, 527) was loaded into the pre-fluorinated weighed FEP tube in a dry box (<1 ppm $H_2O$, supplied by Vacuum Atmospheres Ltd) and 647 mg, 7.614 mmol of $CH_2Cl_2$ were sublimed into the reaction tube. The reaction tube was allowed to warm up to 10° C.

The results are shown in Table 1. From these results it was calculated that the replacement of chlorine by fluorine was 96.5% selective.

EXAMPLE 5

Fluorination of $CH_2Cl_2$ by $UF_6$

The procedure described in example 1 was followed except that 415.0 mg, 1.179 mmol of $UF_6$ (prepared as described in DOKL AKAD NAUK SSSR, 1962, 143) and 1317 mg, 15.5 mmol of $CH_2Cl_2$ were sublimed into the reaction tube. The reaction was allowed to proceed for 5 days before analysis by n.m.r. was carried out. The involatile precipitate was determined to be $UF_5$.

The results are shown in Table 1. From these results it was calculated that the replacement of hydrogen by fluorine was 99.9% selective.

EXAMPLE 6

Fluorination of $CH_2Cl_2$ by $VF_5$

The procedure described in example 1 was followed except that 190.5 mg, 1.305 mmol of $VF_5$ (prepared as described in J. Chem Soc., 1949, 2979) and 942.5 mg, 11.09 mmol of $CH_2Cl_2$ were sublimed into the reaction tube. The FEP tube was allowed to warm up to 0° C. The reaction was allowed to proceed for 2 hours before carrying out analysis by n.m.r. The involatile product was determined to be $VF_4$.

The results are shown in Table 1. From these results it was calculated that the replacement of hydrogen by fluorine was 92.0% selective.

EXAMPLE 7

Fluorination of $CH_2Cl_2$ by $ReF_7$

The procedure described in example 1 was followed except that 207.3 mg, 0.649 mmol of $ReF_7$ (prepared as described in J. Inorg Nucl Chem., 1961, 20, 189) and 1061.3 mg, 12.5 mmol of $CH_2Cl_2$ were sublimed into the reaction tube. The reaction was allowed to run for 1 day before analysis by n.m.r. was carried out. Furthermore, after 1 day no precipitate had formed and the FEP reaction tube itself was sealed as described in example 1 without transferring the volatile products to a second FEP tube.

The results are shown in Table 1. From these results it was calculated that the replacement of hydrogen by fluorine was 96.0% selective.

EXAMPLE 8

Fluorination of $CH_2Cl_2$ by $CrF_5$

This reaction was carried out in the presence of HF as solvent. The procedure of example 1 was followed except that 205.4 mg, 1.397 mmol of $CrF_5$ (prepared as described in J. Inorg Chem, 1985, 24, 2286) was loaded into a large (10 cm × 10 mm outside diameter × 1 mm wall thickness) FEP reaction tube in a dry box. Dry HF was then sublimed into the reaction tube and the mixture of $CrF_5$ and HF was stirred for 18 hours to allow dissolution of $CrF_5$ in the HF. 2086 mg, 24.55 mmol of $CH_2Cl_2$ were then sublimed into the reaction vessel and the reaction mixture was stirred at room temperature for 2 hours. After 2 hours, all the volatile products from the reaction tube were allowed to condense in a large FEP tube which was at −196° C. The volatile products were warmed up to −78° C. in a dry-ice acetone bath and the HF and organic layers were separated by freezing the organic layer at −196° C. and vacuum subliming the HF layer into a further FEP tube. The organic phase was then warmed up to room temperature and vacuum sublimed into a third FEP tube. The FEP tubes containing the organic phase and HF phases were then heat sealed and taken for n.m.r. analysis.

The results are shown in Table 1. The results show that the fluorination of $CH_2Cl_2$ using $CrF_5$ is not selective.

EXAMPLE 9

Fluorination of $CH_2Br_2$ by $ReF_7$

The procedure described in example 1 was followed except that 49.0 mg, 0.1535 mmol of $ReF_7$ and 854.3 mg, 4.91 mmol of $CH_2Br_2$ were sublimed into the reaction tube. The reaction was allowed to run for 1 day before analysis by n.m.r. was carried out. Furthermore, after 1 day no precipitate had formed and the FEP reaction tube itself was sealed as described in example 1 without transferring the volatile products to a second FEP tube.

The results are shown in Table 2. From these results it was calculated that the replacement of bromine by fluorine was 98.0% selective.

EXAMPLE 10

Fluorination of $CH_2Br_2$ by $UF_6$

The procedure described in example 1 was followed except that 217.5 mg, 0.618 mmol of $UF_6$ and 1142 mg, 6.57 mmol of $CH_2Br_2$ were sublimed into the reaction tube. The reaction was allowed to proceed for 14 days before analysis by n.m.r. was carried out.

The results are shown in Table 2. From these results it was calculated that the replacement of hydrogen by fluorine was 100.0% selective.

EXAMPLE 11

Fluorination of $CF_3CH_2Cl$ by $VF_5$

The procedure described in example 1 was followed except that 93.3 mg, 0.639 mmol of $VF_5$ and 464.0 mg, 3.916 mmol of $CF_3CH_2Cl$ were sublimed into the reaction tube, and the reaction was allowed to proceed for 4 days.

The results are shown in Table 3. From these results it was calculated that the replacement of hydrogen by fluorine was 100% selective and that the yield of fluorinated products was 70%.

EXAMPLE 12

Fluorination of $CF_3CH_2Cl$ by $ReF_7$

The procedure described in example 1 was followed except that 151.5 mg, 0.475 mmol of $ReF_7$ and 443.7 mg, 3.74 mmol of $CF_3CH_2Cl$ were sublimed into the reaction tube. The reaction was allowed to run for 1 day before analysis by n.m.r. was carried out. Furthermore, after 1 day no precipitate had formed and the FEP reaction tube itself was sealed as described in example 1 without transferring the volatile products to a second FEP tube.

The results are shown in Table 3. From these results it was calculated that the replacement of hydrogen by fluorine was 100% selective and that the yield of fluorinated products was 26%.

EXAMPLE 13

Fluorination of $CF_3CH_2Cl$ by $RuF_5$

The procedure described in example 1 was followed except that 200.0 mg, 1.021 mmol of solid $RuF_5$ was loaded into the pre-fluorinated weighed FEP tube in a dry box (<1 ppm $H_2O$, supplied by Vacuum Atmospheres Ltd) and 906.9 mg, 7.653 mmol of $CF_3CH_2Cl$ were sublimed into the reaction tube. Reaction was allowed to proceed for 2 hours.

The results are shown in Table 3. From these results it was calculated that the replacement of hydrogen by fluorine was 43% selective. The large amount of $CHF_3$ produced resulted from the fluorination by $RuF_5$ of $CHF_2Cl$ which was present as a reactive contaminant in the $CF_3CH_2Cl$ used.

TABLE 1

PRODUCTS OF FLUORINATION OF $CH_2Cl_2$.

| | TM FLUORIDE | | | | | | |
|---|---|---|---|---|---|---|---|
| | $ReF_7$ | $ReF_6$ | $OsF_6$ | $IrF_6$ | $UF_6$ | $RuF_5$ | $VF_5$ | $CrF_5$ |
| PRODUCTS. MOLE %. (Moles.) | | | | | | | | |
| $CH_2ClF$. | 1.2 | 85.1 (0.5) | 22.1 (0.17) | 42.0 | | 37.4 | 2.0 (0.03) | 27.8 |
| $CH_2F_2$. | | 3.44 (0.01) | 54.8 (0.21) | 29.3 | | 59.1 | | 2.6 |
| $CHCl_2F$. | 43.2 | 4.1 (0.03) | | 11.1 | 99.9 (1.18) | 1.68 | 91.9 (1.18) | 8.17 |
| $CHClF_2$. | 0.6 | 3.2 (0.01) | 1.3 (0.01) | 10.2 | | 1.2 | 6.2 (0.08) | 27.5 |
| $CHF_3$. | | | 7.92 (0.02) | 7.4 | | 0.6 | | 3.0 |
| $CF_2Cl_2$. | | | 0.26 | | | | | 2.0 |
| $CF_3Cl$. | | | 1.67 (0.004) | | | | | 2.4 |
| $CF_4$. | | | | | | | | 4.4 |
| HF. | 54.7 | 4.1 (0.03) | 12.5 (0.1) | | | | | |

TABLE 2

PRODUCTS OF FLUORINATION OF $CH_2Br_2$.

| | PRODUCT/Mole %. | | | |
|---|---|---|---|---|
| | $CH_2BrF$ | $CH_2F_2$ | $CHBr_2F$ | $CHBrF_2$ |
| TM FLUORIDE. | | | | |
| $ReF_7$. | 40.1 | 58.2 | 0.38 | 1.21 |
| $UF_6$. | 85.5 | 14.5 | | |

TABLE 3

PRODUCTS OF FLUORINATION OF $CF_3CH_2Cl$.

| | TM FLUORIDE. | | |
|---|---|---|---|
| | $VF_5$. | $ReF_7$. | $RuF_5$. |
| PRODUCT/Mole %. (No. of Moles). | | | |
| $CF_3CHFCl$. | 100 (0.111) | 100 (0.0299) | 43.0 |
| $CF_3CFCl_2$. | | | 4.8 |
| $CF_3CHCl_2$. | | | 3.0 |
| $CF_3H$. | | | 49.2 |

We claim:

1. A process for the preparation of an alkane containing fluorine which comprises contacting a halogenated alkane containing at least one hydrogen atom and at least one halogen atom selected from chlorine, bromine and iodine with a transition metal fluoride selected from osmium hexafluoride, iridium hexafluoride, rhenium hexafluoride, ruthenium pentafluoride, vanadium pentafluoride and rhenium heptafluoride, and replacing at least one hydrogen atom or at least one chlorine, bromine or iodine atom in said halogenated alkane by a fluorine atom.

2. A process as claimed in claim 1 in which the halogenated alkane comprises a hydrochlorocarbon or chlorofluorohydrocarbon.

3. A process as claimed in claim 2 in which the halogenated alkane is selected from the group consisting of dichloromethane, chlorofluoromethane, dibromomethane, bromofluoromethane, and 2-chloro-1,1,1-trifluoroethane.

4. A process as claimed in claim 1 wherein the halogenated alkane is contacted with $OsF_6$, $IrF_6$ or $ReF_6$ and at least one chlorine, bromine or iodine atom in said halogenated alkane is replaced by a fluorine atom.

5. A process as claimed in claim 1 in which the halogenated alkane is contacted with $VF_5$ or $ReF_7$ and at least one hydrogen atom in said halogenated alkane is replaced by a fluorine atom.

6. A process for the preparation of difluoromethane which process comprises contacting dichloromethane or chlorofluoromethane with a transition metal fluoride selected from $OsF_6$, $IrF_6$, $ReF_6$ and $RuF_5$ and maintaining the contact until at least a portion of the dichloromethane or chlorofluoromethane has been converted to difluoromethane.

7. A process for the preparation of 1,1,1,2-tetrafluoroethane which comprises contacting 2-chloro-1,1,1-trifluoroethane with a transition metal fluoride selected from $OsF_6$, $IrF_6$, and $ReF_6$ and maintaining the contact until at least a portion of the 2-chloro-1,1,1-trifluoroethane has been converted to 1,1,1,2-tetrafluoroethane.

8. A process as claimed in any one of claims 1 to 7 which comprises contacting the transition metal fluoride with the halogenated alkane in the liquid or vapour phase at a temperature in the range from about −80° C. to about 100° C.

* * * * *